United States Patent [19]
Gonzales et al.

[11] Patent Number: 5,846,216
[45] Date of Patent: Dec. 8, 1998

[54] MUCOUS MEMBRANE INFUSOR AND METHOD OF USE FOR DISPENSING MEDICATIONS

[75] Inventors: Gilbert Gonzales, Scottsdale, Ariz.; David A. Easter, Westerville, Ohio; Douglas E. Boyd, Dublin, Ohio; Kenneth E. Hughes, Gahanna, Ohio

[73] Assignee: G & P Technologies, Inc., New York, N.Y.

[21] Appl. No.: 418,580

[22] Filed: Apr. 6, 1995

[51] Int. Cl.$^6$ .................................................. A61M 35/00
[52] U.S. Cl. .................................................. 604/2; 604/49
[58] Field of Search .............................. 604/1, 2, 3, 131, 604/49

[56] References Cited

U.S. PATENT DOCUMENTS

| 467,599 | 1/1892 | Abundi et al. | 604/2 |
|---|---|---|---|
| 2,170,222 | 8/1939 | Strauss | 604/2 |
| 2,491,274 | 12/1949 | McNeill | 604/1 |
| 3,126,006 | 3/1964 | Dowell | 604/1 X |

(List continued on next page.)

FOREIGN PATENT DOCUMENTS

| 263976 | 4/1988 | European Pat. Off. . |
|---|---|---|
| 281212 | 9/1988 | European Pat. Off. . |
| 2516350 | 10/1976 | Germany . |
| WO 81/00356 | 2/1981 | WIPO . |
| WO 89/03232 | 4/1989 | WIPO . |

OTHER PUBLICATIONS

Oscar V. Batson, MA, MD, "The Function of the Vertebral Veins and Their Roll in the Spread of Metastases", Annals Surgery, 1940; 112:138–149.

James E. Eckenhoff, MD, "The Physiologic Significance of the Vertebral Venous Plexus" Surgery, Gynecology & Obstetrics, 1970; 131: 72–76.

Wilson I.B. Onuigbo, "Batson's Theory of Vertebral Venous Metastasis, A Review" Oncology, 32; 145–150/1975.

Hoogdalem et al., "Pharmacokinetics of Rectal Drug Administration, Part I" Clin. Pharmacokinet 21/1c, 11–26, 1991.

Ripamonti et al., "Rectal, Buccal, and Sublingual Narcotics for the Management of Cancer Pain" Journal of Palliative Care 7:Jan. 1991; 30–35.

DeBoer et al., "Drug Absorption by Sublingual and Rectal Routes" British Journal of Anesthesia /1984, 56, 59.

Gonzales et al., "Analgesia Using Vertebral Venous Plexus–Batson' Plexus–Shunting of Rectally" Administered Opoids and Anesthetics to the Central Nervous System; Journal of Pain and Sympton Management, vol. 7, No. 4, May 1992.

Vasant V. Ranade, Ph.D., and Mannfred A. Hollinger, Ph.D., *Drug Delivery Systems*, CRC Press, New York, 1996, pp. 264–284.

*Primary Examiner*—John D. Yasko
*Attorney, Agent, or Firm*—Wood, Herron & Evans, LLP

[57] ABSTRACT

An infusor system for administering medications to a patient comprises a delivery tube with one of the ends couplable to a supply of liquid medication. A dispenser head is coupled to the other end of the delivery tube and medication is directed through the tube to the dispenser head. The dispenser head includes a contact surface and is configured to be placed within a body cavity of a patient such that the contact surface contacts a portion of a mucous membrane in the body. The dispenser head is operable for directing medication from the delivery tube to the contact surface and on to the mucous membrane to be absorbed by the mucous membrane and distributed in a body of a patient. In a preferred embodiment of the invention, the dispenser head includes a portion of compressible foam which is configured to fit within the rectal cavity of a patient. The dispenser head channels, wicks or otherwise directs medication to the rectal mucous membrane to be absorbed thereby. Unique methods of utilizing the infusor system to administer medication to a patient are set forth herein.

22 Claims, 4 Drawing Sheets

U.S. PATENT DOCUMENTS

| | | | |
|---|---|---|---|
| 3,324,855 | 6/1967 | Heimlich | 604/3 |
| 3,368,549 | 2/1968 | Barr et al. | 604/1 X |
| 3,512,526 | 5/1970 | Feilding | 604/2 |
| 4,233,025 | 11/1980 | Larson et al. | 604/1 X |
| 4,471,782 | 9/1984 | Shuffield . | |
| 4,516,578 | 5/1985 | Shuffield . | |
| 4,572,832 | 2/1986 | Kigasawa et al. . | |
| 4,925,327 | 5/1990 | Wirt | 401/205 |
| 4,979,948 | 12/1990 | Goddes et al. . | |
| 5,123,431 | 6/1992 | Wilson | 604/1 X |
| 5,152,724 | 10/1992 | Simpson | 604/3 |
| 5,152,742 | 10/1992 | Simpson | 604/1 |
| 5,158,532 | 10/1992 | Peng et al. | 604/2 X |
| 5,377,874 | 1/1995 | Brown | 604/3 X |

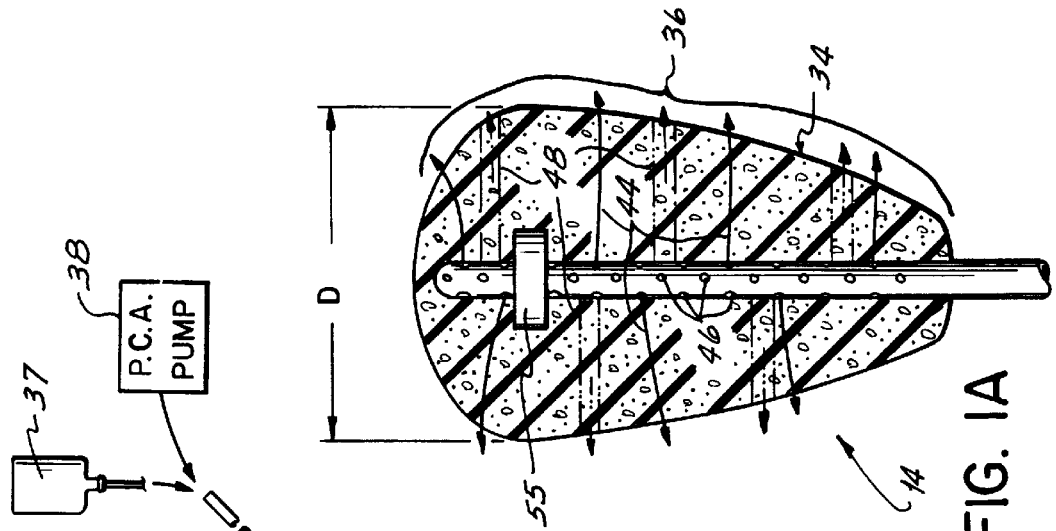
FIG. IA
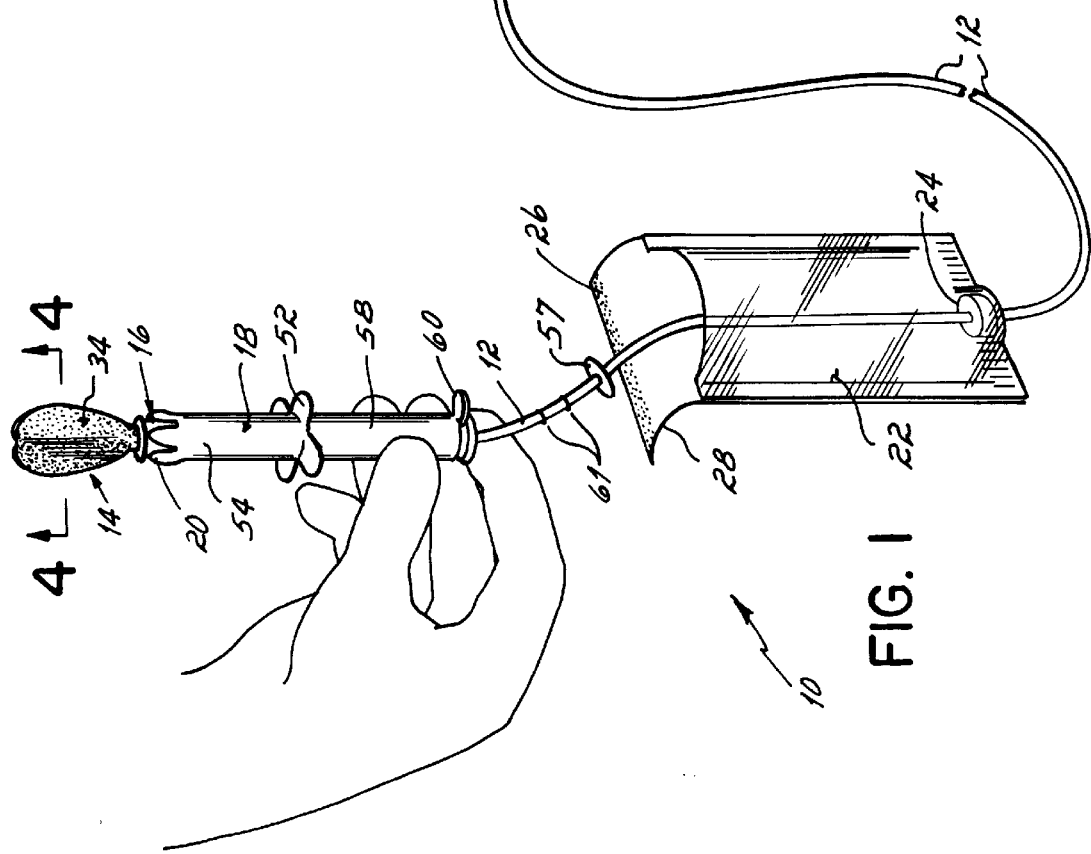
FIG. I

MUCOUS MEMBRANE INFUSOR AND METHOD OF USE FOR DISPENSING MEDICATIONS

FIELD OF THE INVENTION

The present invention relates generally to the administration of medications to patients and specifically to the administration of medications through mucous membranes, and more specifically, the rectal mucous membrane of a patient.

BACKGROUND OF THE INVENTION

The effective administration of medications for the treatment of disease symptoms and for the alleviation of pain, i.e., pain management, is an important aspect of the overall treatment of patients for both curable diseases and terminal illnesses. Particularly, the effective administration of medications in patients experiencing chronic pain associated with a terminal illness is particularly important, because such pain management requires constant administration of medication over prolonged periods of time. As a result, the management of pain for terminally ill patients, such as, terminal cancer patient and those afflicted with HIV has come to the forefront as the medical profession seeks to alleviate pain to allow the patient to comfortably pass away.

Oral administration has been widely utilized in the past for dispensing pain medications such as narcotic and non-narcotic analgesics. However, oral administration is oftentimes not possible due to an obstruction blocking the oral and gastrointestinal tract or due to severe nausea and vomiting by the patient. Such gastrointestinal problems are often experienced by terminally ill patients whose bodies are slowly deteriorating.

Parenteral administration or administration outside of the intestine, such as through bolus injections or slow infusions are also widely utilized. Intravenous (I.V.) drips are particularly popular for long term administration of a medication in controlled dosages. However, parenteral administration is invasive and usually painful to the patient. Undesirable local reactions can occur at the sight of the injection or the infusion, and wheal or skin elevation occurs due to the injections or infusions which involve a needle and are subcutaneous or beneath the skin. Furthermore, parenteral administration of medications may not be possible if there is a lack of peripheral vasculature and blood flow cannot move to certain areas of the body. Also, some terminally ill patients may refuse parenteral administration of medications.

Parenteral administration of medications is also not practical for long-term patient care due to the requirement that proper injection sights must be utilized for effective administration. Terminally ill patients may not have the physical capability of performing an injection procedure, and if physically able, may not have the knowledge to properly chose an injection site and administer the medication. Thus, while parenteral administration may be effective, a properly trained health-care provider is usually necessary for administration. When long term patient care must be provided by an untrained person, injection techniques may become impossible to implement requiring a patient to stay within a hospital or other medical facility indefinitely. Therefore, alternative methods of administration that are less complex and demanding are desirable.

To that end, rectal administration of medication has presented a practical alternative and is now widely used for delivering a number of different medications, including non-narcotic and narcotic analgesics for pain management, anti-nausea medications, and steroids. Other medications which may be administered rectally include: antibiotics, chemotherapy, antipyretics, anesthetics, laxatives, and non-steroidal antiinflammatory agents, among others. A suppository of medication is placed within the rectum and dissolves while dispensing the medication. Rectal administration is generally non-invasive and not painful. Furthermore, a large amount of currently available experience in rectal administration of medications makes the method very safe. For long-term care, rectal administration is inexpensive because it requires fewer caretakers, less skilled caretakers and generally less monitoring as the medication is dispensed. Since the environment of the rectum is fairly constant, it favors a reproducible absorption process. Furthermore, the absorption of medication, which occurs through the rectal mucous membrane, provides slow, continuous release for an extended time period.

However, currently available rectal administration techniques involve the use of suppositories which contain a fixed dosing of medication. The suppositories are placed within the rectum for onetime, slow and continuous absorption. Therefore, there is generally no control over the administration rate except that provided by the fixed breakdown of the suppository and the absorption rate of the rectal mucous membrane. As such, suppositories do not provide the needed flexibility in the management of pain which often requires quick bolus administrations to combat acute pain and acute worsening of pain. Furthermore, since suppositories are generally single dose elements, extended care may require the continual insertion of single dose suppositories for continuous pain management. Such continuous monitoring is expensive and often requires a skilled caregiver when the patient is either unable or unwilling to insert the suppository.

For pain management, the intraspinal administration of non-narcotic and narcotic analgesics is important in alleviating acute and chronic pain. Approaches have been developed for delivering high concentrations of medications into the spinal cord; however, all such techniques are invasive and have associated risks related to the use of a catheter or pump for the injection of infusion. Furthermore, most of these techniques are generally expensive as they require administration and monitoring by skilled medical personnel.

Recently, the use of the reversal of blood flow in the vertebral venous system or Batson's Plexus for rectal administration of medications has shown promise as a method of administering analgesics and anesthetics at high concentration directly into the intraspinal areas. Reversal of flow in the Batson's Plexus refers to the physical phenomenon of reversal of blood flow in the veins of the vertebral structures when intraabdominal pressure is applied. Normally, the vertebral venus plexus in the pelvis, sacrum and lumbar spine assist in carrying the venus blood from the meningorrhaachidian veins of the vertebral structures, including the spinal cord, to the sacrum and sacral plexus, the iliac veins and ultimately to the inferior vena cava and to the heart. However, the vertebral venus plexus or Batson's plexus is valveless so blood is free to flow in any direction. The Batson effect occurs upon increased intraabdominal pressure which causes reversal of pelvic and lumbar venus flow such that venus flow occurs from the sacral venus plexus and inferior vena cava into the meningorrhaachidian blood vessels. In short, normal blood flow occurs from the spinal column toward the heart, but under Batson's described effect, blood flow can occur in the opposite direction, providing blood flow back to the spinal area. Using Batson's plexus reverse flow by increased intraabdominal pressure, in conjunction with the administration of analgesics using a rectal suppository, the analgesic might be more efficiently and effectively administered at high concentrations to the spinal cord to alleviate pain without infusions. However, such a method is subject to the inherent drawbacks of suppository use discussed above, including the lack of control over the dosage rates as well as the requirement of constant insertion of the suppositories as they are used. Additionally, the administration of bolus amounts of medication for acute pain is not possible with suppositories. Furthermore, such rectal administration may be subject to greater partial metabolization and elimination of the analgesics by the liver as major rectal veins in the more internal end of the rectum where the suppository would be located drain into the liver.

Therefore, it is an objective of the present invention to administer medications to patients without the various drawbacks associated with traditional oral and parenteral methods of administration discussed hereinabove. Furthermore, it is an objective to administer medication rectally with greater flexibility than provided with currently available rectal techniques.

Particularly, it is an objective of the present invention to administer non-narcotic and narcotic analgesics to continuous care and terminal patients for the management of acute and chronic pain.

It is a further objective of the present invention to administer medications in a non-painful, non-invasive and safe way without incurring the large expense associated with procedures involving administration and continual monitoring by large numbers of skilled caretakers, such as physicians and nurses. Safe, effective and inexpensive pain management in economically depressed, third world countries is particularly important, as these countries often have large numbers of terminally ill patients without the requisite medical staff available.

It is a further objective of the present invention to provide greater flexibility in the administration of medications, both continuously and in bolus dosages and to provide for easy initiation and termination of the dispensing process.

It is a further objective to administer medications so that the medications are rapidly and efficiently absorbed into the necessary areas of the body to alleviate the medical condition or the pain associated therewith.

It is also an objective of the present invention to more efficiently and effectively administer medications into the intraspinal area and particularly to administer anesthetics and analgesics into that area for pain management purposes.

SUMMARY OF THE INVENTION

The above-discussed objectives are addressed in the present invention which comprises an infusor system for administering medications to a patient through a body cavity containing a mucous membrane. In a preferred embodiment of the invention, the infusor system is designed for use within the rectal cavity of a patient for administering medications through the rectal mucous membrane and into the body of the patient.

In a preferred embodiment, the infusor system comprises a compressible, porous foam dispenser head configured for placement within the rectal cavity of a patient. The dispenser head includes one or more contact surfaces which contact a portion of the rectal mucous membrane in the body. The system further comprises a delivery tube coupled at one end to a supply of liquid medication and at an opposite end to the dispenser head. The opposite tube end is preferably surrounded by the dispenser head and includes a plurality of apertures which create a medication flow into the dispenser head and the porous dispenser head is operable for directing the medication from the delivery tube to the contact surface and onto the mucous membrane to be absorbed thereby. In one embodiment, the porous dispenser head is made of an open-cell foam and wicks the medication to the contact surface. In another embodiment, the head is made of a closed-cell foam which has a series of radial passages to direct the medication to the contact surface. A wicking membrane might be utilized at the contact surfaces for more efficient transfer of the medication to the mucous membrane.

The supply of medication is delivered into the tube and to the tube dispenser head either continuously through an I.V. drip bag or a pump apparatus or in a bolus dosage. To that end, the infusor system includes apparatus for coupling the tube to an I.V. bag or to a pump and also includes a bolus injection site. The infusor system further comprises a one-way valve in the delivery tube for allowing medication flow in only one direction, from the supply to the dispenser head.

The dispenser head is compressible and is held within an elongated applicator sheath in a compressed state before it is inserted into the body cavity. A plunger is coupled to one end of the dispenser head and is slidably moveable within the sheath to push the dispenser head out of the sheath when the applicator sheath has been inserted into the body cavity. The dispenser head then expands from the compressed state to maintain the contact surface in positive contact against the mucous membrane. A depth indicator positioned on the sheath indicates the desired insertion depth of the applicator sheath in the body cavity for proper location of the dispenser head against the mucous membrane.

The sheath includes a tear away section which may be torn away so that the applicator sheath may be split longitudinally to be removed from the tube and dispenser head. Furthermore, the plunger is also preferably split longitudinally for removal from the delivery tube and dispenser head after the dispenser head is positioned in the body cavity and the sheath is removed. Therefore, when the infusor system is utilized, only the dispenser head and medication delivery tube extending therefrom remain within or proximate to the body cavity. Medication delivered through the tube and the dispenser head is then absorbed by the mucous membrane. A disposal package is slidably mounted to the delivery tube and is configured for being slid around the used dispenser head after it has been removed from the body cavity. The disposal package is then sealable with the dispenser head therein for safe disposal.

In an alternative embodiment of the invention, a dispenser head comprises an elongated coil portion which is coupled to the medication delivery tube. The coiled portion is compressed within the applicator sheath and has a physical memory of its expanded shape. When the sheath has been slid away from the coil portion, the coil portion returns to its expanded shape to provide a contact surface against the mucous membrane. Perforations within the coiled portion dispense the medication from the delivery tube to the mucous membrane.

In another alternative embodiment of the invention, the dispenser head includes a porous fiber core which surrounds an end section of the delivery tube which has a plurality of apertures therein. The medication is dispensed into the core through the tube apertures and is absorbed by the core. A shell which is generally stiffer than the core surrounds the core and makes contact with the mucous membrane. A plurality of apertures are formed in the shell and medication is dispensed from the tube through the core and through the shell to be absorbed by the mucous membrane. Surrounding the tube generally coaxially with the core is a ferrous plastic material utilized to secure the dispenser head within the body cavity. The infusor system comprises a magnetic securing element which is placed on the patient's body proximate the body cavity containing the dispenser head. The magnetic attraction between the magnetic element and the ferrous material in the dispenser head holds the dispenser head within the body cavity to make positive contact with the mucous membrane.

The dispenser head and delivery tube of the present invention are flexible and therefore comfortable to the patient. Furthermore, the rectal administration of medications with the infusor system is safe. Additionally, the rectal mucous membrane has good absorption, and since the medication is dispensed through a mucous membrane, the various drawbacks associated with traditional oral and parenteral methods of administration are eliminated, including the necessity of properly preparing and monitoring an injection site and side effect and skin wheal from injections.

Using the infusor system of the invention, the rate of medication administration can be flexibly controlled by varying the rate of medication delivery to the dispenser head. Therefore, when utilized rectally, the infusor system provides greater flexibility and dosing than is provided by the present rectal administration procedures utilizing suppositories. The invention provides for better pain management with patient's experiencing acute pain and acute worsening of pain. Non-narcotic and narcotic analgesics can be easily administered to continuous care and terminal patients in a generally non-painful, medically non-invasive and safe manner.

The infusor system eliminates the large expenses associated with other procedures which involve administration and continual monitoring by professional medical personnel. The dispenser head of the infusor system may be inserted into the body cavity, such as the rectal cavity, and left therein while medication is supplied. Furthermore, medication administration can be easily initiated and terminated by simply starting or stopping the flow of medication to the delivery tube and the dispenser head. The infusor system provides safe, effective and inexpensive pain management and is particularly useful in economically depressed third-world countries which have large numbers of terminally ill patients who do not have the monetary resources to afford continuous attention by medical professionals, even if such professionals are available. The medications dispensed through the infusor system are rapidly and efficiently absorbed into the necessary areas of the body for alleviation of the medical condition or the pain associated therewith. Furthermore, a large number of medications may be introduced through the rectal mucous membrane, such as chemotherapy medications and some anesthetics.

An inventive rectal method of use of the infusor system is particularly effective for the efficient administration of medications directly into the intraspinal area for pain management. The infusor system is utilized within the rectal cavity by positioning the dispenser head in the rectal cavity adjacent to the mucous membrane. Medications dispensed through the head are absorbed by the rectal cavity mucous membrane and are utilized within the body. In accordance with one method of use of the invention, the rectal infusor is placed in the innermost (upper) end of the rectal cavity away from or furthest from the anus, and medications are absorbed by the mucous membrane and carried by blood in the superior rectal vein to the liver to be metabolized and utilized within the body.

In an alternative embodiment of the inventive method, the applicator sheath is positioned within the rectal cavity to locate the dispenser head generally in the external (lower) two-thirds of the length of the rectal cavity. That is, the dispenser head is placed in the rectal cavity near the anus. The dispenser head is preferably placed proximate the portion of the mucous membrane which is drained by the middle and inferior rectal veins which return blood directly to the inferior vena cava and then to the heart. As such, the medications absorbed are delivered for systemic circulation within the body, bypassing the liver and avoiding first-pass metabolism within the liver. Accordingly, a greater percentage of the dispensed medication, such as an analgesic, is available for use by the body to handle pain or to alleviate any other symptom to which the medication is directed.

In still a further alternative embodiment of the inventive method, the dispenser head is placed within the internal two-thirds of the rectal cavity and medication is dispensed. Intraabdominal pressure is then increased by any number of a different available methods, such as by utilizing an abdominal restraint or binder. The blood flow in the vertebral venus plexus is reversed and the dispensed medication is delivered from the rectal and sacral veins directly into the vertebral bones, the epidural and intrathecal space and the spinal cord. By maintaining the increase in the intraabdominal pressure long enough, cranial structures will also receive the vertebral venus flow of medication.

Therefore, the infusor system of the present invention provides a more direct infusion of medication, either continuously or in bolus dosages, into the spinal cord and other vertebral structures, as compared to oral or parenteral administration, for more effective pain management. As such, analgesic medication, such as morphine, can be delivered in relatively higher concentrations to the spinal cord before circulating throughout the body and before significant dilution. Furthermore, the bypassing of liver metabolism provides a greater concentration of available medication to the necessary targeted areas. Since there are lower concentrations of the analgesics dispensed systemically within the body, side effects such as sedation, respiratory depression, nausea and vomiting are reduced. Still further, utilizing the inventive method of the present invention, more costly injection procedures requiring skilled professionals are avoided when introducing medications within the epidural and intrathecal spaces of the spinal column.

These advantages and other advantages and objectives of the present invention will become more readily apparent below from the Brief Description of the Drawings and the Detailed Description of the Invention.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a schematic view of an embodiment of the infusor system of the invention;

FIG. 1A is an enlarged view, in partial cross-section, of the dispenser head of the infusor system of FIG. 1;

FIG. 7A is a side cross-sectional view of an alternative embodiment of the dispenser head of the invention shown compressed within the applicator sheath, while

DETAILED DESCRIPTION OF SPECIFIC EMBODIMENTS

Figure 2:
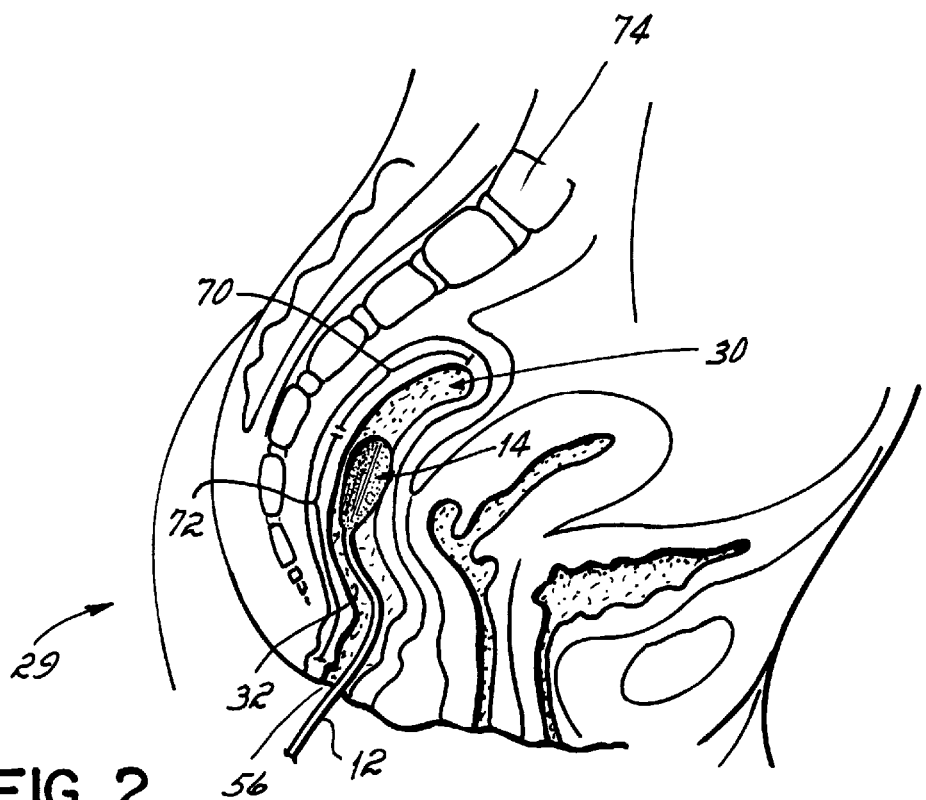
FIG. 2 is a side view, in partial cross-section, of a patient body illustrating the infusor system used within the rectal cavity of the body.

FIG. 1 is a schematic view of a preferred embodiment of infusor system 10 of the present invention. Infusor system 10 includes a medication delivery tube 12, which is coupled to a supply of medication to be dispensed therethrough. The tube 12 may be made of PVC material or of a biodegradable material for more environmentally safe disposal. Delivery tube 12 is coupled to a dispenser head 14 for dispensing medication delivered thereto by tube 12. As discussed further hereinbelow, the dispenser head 14 is operable to direct medication from the end of the tube 12 to the mucous membrane of a body cavity.

The dispenser head 14 is also coupled at one end to a plunger 16 for slidably moving the dispenser head 14 within an applicator sheath 18. The applicator sheath 18 is elongated and contains the dispenser head 14 in a compressed state (not shown) while the applicator is inserted into a body cavity containing a mucous membrane, such as the rectal cavity 30 (See FIG. 2). Sheath 18 has a split end 20, which spreads apart and allows the dispenser head 14 to be pushed therethrough when plunger 16 is moved with respect to sheath 18. Once the dispenser head 14 has been inserted into the body cavity the sheath 18 and plunger 16 can be removed as described further hereinbelow. A disposal package 22 is slidably coupled to delivery tube 12 by a rubber or foam gasket seal 24. When the dispenser head 14 has been used and withdrawn from the body cavity, the disposal package 22 may be slid up along the length of tube 12 to thereby receive the dispenser head 14. An adhesive strip 26 on a seal flap 28 of disposal package 22 seals the flap 28 against package 22 for safe disposal of the used dispenser head 14.

Figure 4:
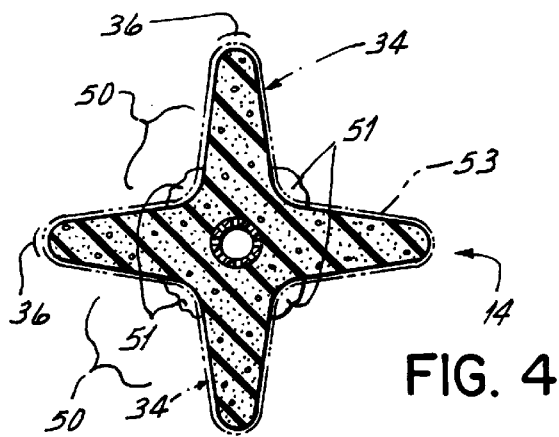
FIG. 4 is a cross-sectional view along lines 4—4 of the dispenser head of FIG. 1.

Referring now to FIG. 2, the dispenser head 14 is shown inserted into the rectal cavity 30 of a patient body 29. Within the rectal cavity 30, the dispenser head 14 contacts mucous membrane 32 of the rectal cavity 30. The dispenser head 14 has at least one contact surface which will contact mucous membrane 32 when the dispenser head has been inserted into the rectal cavity 30 to dispense medication which is then absorbed by the membrane 32. FIG. 4 illustrates a cross-sectional view of one embodiment of the dispenser head 14 which has a generally star-shaped or stellate cross-section with four longitudinal fins 34 which define elongated contact surfaces 36 at the ends thereof for contacting the mucous membrane 32.

As illustrated in FIG. 1, the delivery tube 12 is coupled to a supply of medication and delivers medication to the dispenser head 14 from the supply. For example, the end of the delivery tube 12 opposite the dispenser head 14 might be coupled to an I.V. drip bag 37 for continuously dispensing medications at a controlled drip rate into tube 12. Alternatively, the tube 12 might be connected to a pump device, such as a Patient Controlled Analgesia or P.C.A. pump 38 for injecting medication into tube 12 at a predetermined pumping rate.

Tube 12 also preferably includes a bolus injection dock 40 for receiving a syringe 42 to rapidly inject bolus dosages of a medication to be dispensed through dispenser head 14, such as to alleviate acute pain or acute worsening of pain experienced by a patient utilizing the infusor system 10. A one way valve 41 ensures that medication flows in the proper direction to head 14.

Referring to FIG. 1A, medication is carried by tube 12 to the dispenser head 14. In one embodiment of the invention, the dispenser head 14 is formed of a light-weight, polyurethane foam, which is porous and is operable to direct medication from the tube 12 outwardly to the elongated contact surfaces 36 in the direction of arrows 44. The tube end coupled to dispenser head 14 includes a plurality of apertures 46 formed therein, which create a flow of medication from the tube 12 to permeate into the dispenser head 14. Alternatively, tube 12 might include an open end (not shown) which would simply drain into dispenser head 14 to saturate the dispenser head and provide medication to contact surfaces 36. Preferably, the dispenser head has an effective diameter D such that the contact surfaces 36 are in positive contact with the mucous membrane 32 of the rectal cavity 30 (See FIG. 2). The foam of dispenser head 14 could be an open-cell foam which wicks the medication from the tube end to the contact surfaces 36. Alternatively, a closed-cell foam might be utilized and passages 48 may be formed to direct medication radially outwardly to the contact surfaces 36. A dispenser head 14 using radial passages 48 will tend to minimize the amount of medication which is trapped in the head 14 and therefore not dispensed. As will be appreciated, an open-cell foam which must first be filled or saturated, will contain a certain amount of residual medication which is not used.

The preferred embodiments of the infusor system illustrated herein utilize dispenser heads which are designed and configured to be positioned within the rectal cavity 30. However, the infusor system 10 might also be utilized with other body cavities, either natural or surgically formed, which are adjacent mucous membranes for absorbing medication. For example, the dispenser head 14 of the infusor system 10 might be placed within a vaginal cavity for the absorption of medication by the vagina. Furthermore, the dispenser head 14 might be placed intracolostomy within an opening formed in the large intestine or intraileostomy, within a hole in the small intestine or intragastrostomy within a hole in the stomach. Still further, the infusor system 10 of the present invention might be utilized in the mouth to contact the oral mucous membrane for infusion of medications thereby.

The dispenser head 14 of the invention is illustrated in the Figures is light weight and uniquely shaped to be placed within the rectal cavity 30 to dispense medication. The star-shaped or stellate shape of the dispenser head 14 illustrated in FIG. 4 provides a plurality of longitudinal contact surfaces 36 with defined longitudinal troughs 50 positioned therebetween. When the dispenser head 14 is in a compressed state within sheath 18, the fins 34 of the head are wrapped around the center of the head 14 and tube 12, preferably all oriented in either a clockwise or counter-clockwise direction (not shown). The compressed dispenser head is then held within applicator sheath 18. The person inserting the head 14 positions the sheath 18 within the body cavity. They then expand the head 14 to make contact with mucous membrane 32. As illustrated, in a preferred embodiment of the invention, the head 14 is generally resilient and will expand to the desired shape and size when the sheath 18 is withdrawn. Alternatively, the head 14 might have to be actively expanded such as with a pump system (not shown). When the sheath 18 is withdrawn, such as by pressing dispenser head 14 out of the split end 20 of the sheath 18 by pushing plunger 16 into the sheath, the dispenser head 14 expands to the stellate shape illustrated in the Figures.

Figure 3:
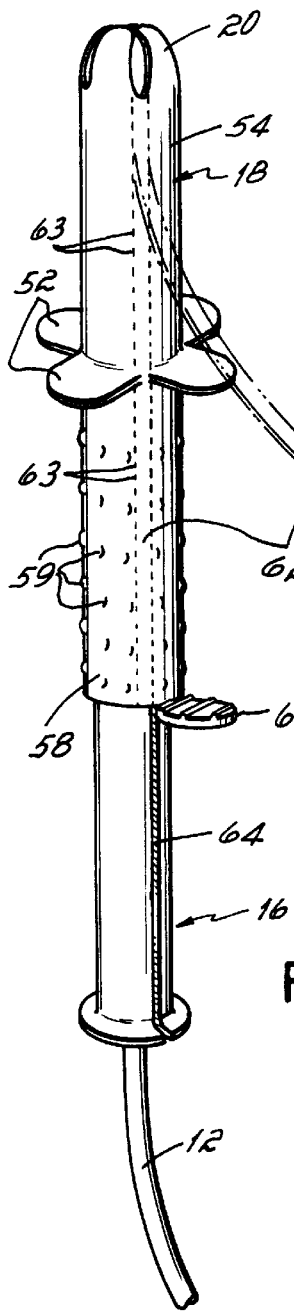
FIG. 3 is a perspective view of the applicator sheath and plunger of the invention for inserting the dispenser head into a body cavity.

Referring to FIG. 3, sheath 18 preferably includes peripheral tabs 52 which set the insertion depth of the top section 54 of sheath 18. The top section 54 is smooth for easy insertion into the rectal cavity through the anus 56 (FIG. 2). The top section 54 might be lubricated with a suitable lubricant for easy insertion into cavity 30. The bottom section 58 of sheath 18 includes a plurality of dimples 59 to provide a gripping surface for fingers when plunger 16 is pushed into sheath 18 to eject the dispenser head 14.

The unique shape of the dispenser head with the alternating contact surfaces 36 and troughs 50 insures positive contact against the mucous membrane 32 of the rectal cavity 30 to provide efficient transfer of medication to membrane 32 and to hold the head 14 in place in cavity 30. Furthermore, the longitudinal fins 34 of the dispenser head 14 are dimensioned in depth such that the contact surfaces 36 make positive contact with mucous membrane 32 without penetrating or otherwise tearing the delicate lining of the mucous membrane 32. A wicking membrane 53 might be utilized to further create efficient transfer of medication from the dispenser head 14 to the mucous membrane 32. As medication is dispensed through tube apertures 46, it is directed radially outward from the tube as illustrated in FIG. 1A, and is also carried longitudinally along the length of head 14 by the troughs 50. FIG. 4 illustrates the medication 51 moving along troughs 50. As the medication spreads throughout the dispenser head, the dispenser head is operable to direct the medication to the contact surfaces 36 for application to the mucous membrane 32. Since the dispenser head 14 is lightweight and will preferably remain generally static within the rectal cavity once it has expanded from its compressed state, the dispenser head has minimal effects on the nerve endings in the rectal cavity. Therefore, the body preferably does not sense the dispenser head 14 as a stool and, therefore, will not react or respond to expel it from the rectal cavity 30. However, should a bowel movement occur, the stool would push the dispenser head out of the rectal cavity as desired. The unique shape and operation of the dispenser head 14 also insures that gas within the system can pass through the rectal cavity 30 and out of the anus 56 without dislodging the dispenser head 14. The gas passes around the longitudinal troughs 50 while the contact surfaces 36 remain in positive contact with the mucous membrane 32.

Although preferably porous to direct medication from tube 12 to the contact surfaces, the material utilized to form the dispenser head should not absorb and hold the medication away from membrane 32. Furthermore, the material should preferably not foster the growth of microflora. While the infusor system 10 of the present invention utilizes a dispenser head 14 which is preferably configured for remaining unobtrusively within the body cavity, it may be useful to precede the insertion of the dispenser head 14 with an anesthetic in the body cavity to prevent immediate expulsion of the head as a foreign body. Furthermore, as mentioned above, the dispenser head is preferably coated with an appropriate lubricant or oil such as paraffin oil or silicon oil to facilitate easy insertion of the dispenser head.

Should it be undesirable to use the sheath and plunger system illustrated in one embodiment of invention. The dispenser head 14 might be positioned within the body cavity by a caregiver, such as using a gloved finger. To aid in the insertion of the dispenser head and positioning at the proper location for infusion, the delivery tube 12 preferably includes a depth marker such as a rib or ring 57 on the delivery tube for indicating to the user that the dispenser head has been located at the right position within the body cavity for proper positioning of the contact surfaces against the mucous membrane. Alternatively, a section of the delivery tube might be color coated. For example, the section of tube between the marker 57 and dispenser head 14 might be a different color than the remaining section of the tube from the marker 57 back to the medication supply. Furthermore, a radio-opaque marker 55 might be coupled to head 14 for detecting, with suitable electronic detection equipment, the installed position of the head relative to the body cavity and the mucous membrane, or the tubing 12 may be impregnated with radio-opaque marks 61 along its length.

The dispenser head 14 is preferably dimensioned approximately 2½ cm in length and preferably should sustain a flow rate of medication suitable for the mucous membrane being utilized. For example, for rectal morphine usage, a sustained flow rate of 15–20 cc/hour at a morphine concentration of 5 mg/cc may be desired. Furthermore, the dispenser head 14 should have the capability of providing bolus dosage delivery of 10–20 cc/hour either as a single dose or in multiple fractions of 20 cc/hour.

After use, the device is preferably purged with 5–10 cc of water to expel and wash out unused drug. The dispenser head 14 is further pliable enough to deform to a compressed state and a smaller effective diameter when it is removed from the body cavity, such as by being pulled through the anal sphincter (not shown) of the anus 56. Preferably, the dispenser head 14 is colored a special color, such as a dark yellow, to reduce the soiled appearance of the dispenser head 14 when it is removed. For rectal use, the dispenser head 14 should be changed at the time of bowel movement up to a maximum time of once every three days. If at three days or sooner, the patient has not experienced a bowel movement, the dispenser head 14 should be removed and a bowel movement may be induced.

The elements of the infusor system should preferably be able to withstand gamma radiation for the purpose of pre-use sterilization. Furthermore, the materials are preferably safe to use in the presence of medical diagnostic systems such as magnetic resonance imaging (MRI), X-ray, or computerized tomography (CT Scan). However, the alternative version of the dispenser head discussed below which utilizes ferrous material may have an effect on such imaging techniques.

Referring again to FIG. 3, the applicator sheath 18 is preferably formed of polyethylene, while the plunger 16 is preferably an impact resistant polystyrene. The sheath 18 and plunger 16 of the invention are preferably dimensioned so that the dispenser head 14 may be properly located within a chosen body cavity. The dimension and length of the sheath and plunger will therefore depend upon the chosen body cavity. Applicator sheath 18 includes a pull tab 60 connected to a longitudinal tear away strip 62 formed by perforations 63 along the length of the sheath 18. Pull tab 60 is pulled away from sheath 18 as illustrated in phantom in FIG. 3 to tear away the strip 62. When the strip 62 is torn away, a longitudinal slit is left on the sheath 18 to allow for easy removal of the sheath from the plunger 16 and tube 12. The plunger 16 also has a pre-formed longitudinal slit 64 which allows the plunger to be spread marginally along the slit so that the plunger 16 may also be removed from around the tube 12 once the inserter head 14 has been inserted into the rectal cavity 30. The sheath and dispenser tube can then be properly disposed leaving only the dispenser head 14 and a portion of the tube 12 within the rectal cavity 30. When the infusion system has been used and the dispenser head 14 has been removed from rectal cavity 30, disposal package 22 is slid along a length of tube 12 to receive the dispenser head 14 for disposal. The seal 24 is used to wipe the tube 12 clean prior to disposal within bag 22. The tube 12 then preferably detaches from the head 14 and is placed in the bag 22.

Medication dispensed through the dispenser head 14 is absorbed by mucous membrane 32 and distributed throughout the body to address a targeted symptom or to alleviate pain experienced by the patient 29. Since the infusor system 10 of the invention is utilized within a formed body cavity, it is non-invasive and generally non-painful. Since no injection is involved, use of the infusor system of the invention is not accompanied by the various drawbacks and side effects experienced with parenteral administration. Furthermore, the infusor system 10 may be utilized with patients who cannot handle orally administered medications. The infusor system provides great flexibility in the dispensing of medication through I.V. bags 37 and pumps 38. A bolus dosage of medication, such as a dosage of morphine for a patient suffering acute pain, can be administered through the bolus dock 40 and received by direct absorption through mucous membrane 32. The bodily absorption of medication through the rectal mucous membrane 32 has proven to be similarly effective as the absorption of medication which has been orally administered.

The infusor system is safe and inexpensive. Not only will the infusor system be generally inexpensive to manufacture, but it is also generally inexpensive to utilize. Once the dispenser head 14 has been properly placed within the rectal cavity 30, it can be left therein to provide continuous medication without the need for constant medical attention, which is often associated with parenteral administration. Furthermore, the infusor system provides continuous dispensing, unlike individual pills or suppositories, which the patient or medical professional must remember to administer at predetermined intervals.

A large number of medications, such as chemotherapy, steroids, anesthetics, opioids, and other narcotic and non-narcotic analgesics may be administered utilizing the infusor system 10 of the present invention. The infusor system is particularly useful for rectally administering analgesics to terminally ill patients for pain management. During operation of the infusor system, it is easy to initiate the administration of medication simply by providing medication flow through tube 12 and into dispenser head 14. Similarly, stopping the medication flow will terminate the administration whereupon it can simply be reinitiated by again beginning the flow through delivery tube 12.

In accordance with one inventive method for utilizing infusor system 10, the dispenser head 14 is positioned in the proximal or most internal one-third (⅓) of the rectal cavity 30 as illustrated by reference numeral 70 in FIG. 2. This section is referred to as the rectum proper. Medication from dispenser head 14 is absorbed by the mucous membrane 32 in the rectum proper 70. The rectum proper 70 is perfused and drained by the superior rectal vein (not shown) which drains into the portal vein, and subsequently into the liver. In the liver, the administered medication is partially metabolized and distributed throughout the body. The rectum proper is generally not as sensitive to the placement of the dispenser head 14 as is the far distal end of the rectal cavity 30 proximate the anus 56. Therefore, the body 29 will generally sense only the thin delivery tube 12 in the anal region, and will adapt to the minor discomfort of the tube 12 without seeking to expel dispenser head 14.

In accordance with an alternative embodiment of the inventive method, the dispenser head is positioned in the distal two-thirds (⅔) of the rectal cavity 30 illustrated by reference numeral 72 in FIG. 2. The distal or outermost two-thirds of the rectal cavity is often referred to as the ampulla and is also generally less sensitive than the area directly proximate anus 56. Therefore, the body should not seek to expel the dispenser head 14 when placed within the ampulla 72 and the anal region will adapt to tube 12. A distinct advantage in locating the dispenser head 14 in the ampulla 72 is that the ampulla is generally drained by the middle and inferior rectal veins (not shown) which return venous blood to the inferior vena cava. In accordance with the principles of the invention, the medications dispensed in the ampulla are delivered to the systemic circulation of the body through the inferior vena cava, thereby bypassing the liver. As a result, the metabolism of the medication in the liver, referred to as first-past metabolism, is avoided, and therefore, low medication metabolism occurs providing greater medication concentration systemically in the body for more effectively address specific symptoms and pain.

In still a further alternative embodiment of the inventive method, use of the infusor system 10 is combined with intraabdominal pressure to infuse medication directly into the spinal structure 74 and the cavity surrounding the spinal structure. The administration of medication directly into the intraspinal area, and particularly, the administration of opioids and other analgesics, is very useful for pain management. For effective intraspinal administration in accordance with the principles of the present invention, the dispenser head 14 is positioned within the ampulla 72 to deliver medication to the mucous membrane 32. Intra-abdominal pressure is then increased to create a reversal of blood flow within the vertebral venous plexus or Batson's plexus. The intra abdominal pressure may be applied such as by using an abdominal restraint or binder or any other medically suitable method for creating intra-abdominal pressure. The Batson's plexus is valveless and blood is free to flow in the reverse direction when intra-abdominal pressure is applied. Normally, the vertebral venous plexus in the pelvis, sacrum and lumbar spine assist in carrying the venous blood from the meningorrhaachidian veins of the vertebral structures 74, including the spinal cord, to the sacrum and sacral plexus, the iliac veins and ultimately to the inferior vena cava and to the heart. However, upon the reversal of pelvic, sacral, and lumbar venous flow, the venous flow occurs from the sacral venous plexus and into the meningorrhaachidian blood vessels, That is, the normal blood flow that occurs from the spinal column toward the heart reverses in the reversal of flow in the Batson's plexus such that blood flow occurs back into the spinal area. Therefore, using Batson's plexus reverse flow with the infusor system 10 in accordance with the principles of the present invention, medications are absorbed by mucous membrane 32 and more effectively and efficiently administered to the spinal cord, such as to alleviate pain. As an example, morphine administered utilizing infusor system 10 with increased intra-abdominal pressure, is delivered in high concentrations to the spinal cord and other vertebral structures.

Minimal systemic dosing of the morphine or other medication occurs utilizing the inventive method, and thus, it provides a number of distinct advantages. Concentrated medications, such as analgesics, are delivered into the spinal cord and other vertebral structures 74 before circulating throughout the body and before significant dilution occurs. Furthermore, the medications are directly delivered into the vertebral structures before liver metabolism of the medication occurs. With a greater concentration of the medication directed to the vertebral structures instead of systemically throughout the body, side effects such as sedation, respiratory depression, nausea, and vomiting are reduced because there are lower concentrations of the medication to the brain and brain stem. Furthermore, utilizing the inventive method, the delivery of medications can be given intermittently, if desired, into the vertebral venus plexus using intermittent intraabdominal pressure, and then a systemic delivery can be initiated simply by removing the intraabdominal pressure. Therefore, high concentrations of an analgesic might be infused intraspinally to handle acute pain, and then systemically for continuous management of less acute, chronic pain. A further advantage of the inventive method is that medication may be administered epidurally, that is, outside of the covering of the spinal cord, and intrathecally, that is, within the spinal fluid surrounding the spinal cord, without the use of injections, which are generally costly and usually require administration by a trained anesthesiologist due to potential risks and also require continuous monitoring by trained personnel. Therefore, the cost of effective pain management and the risks are reduced.

Figure 5:
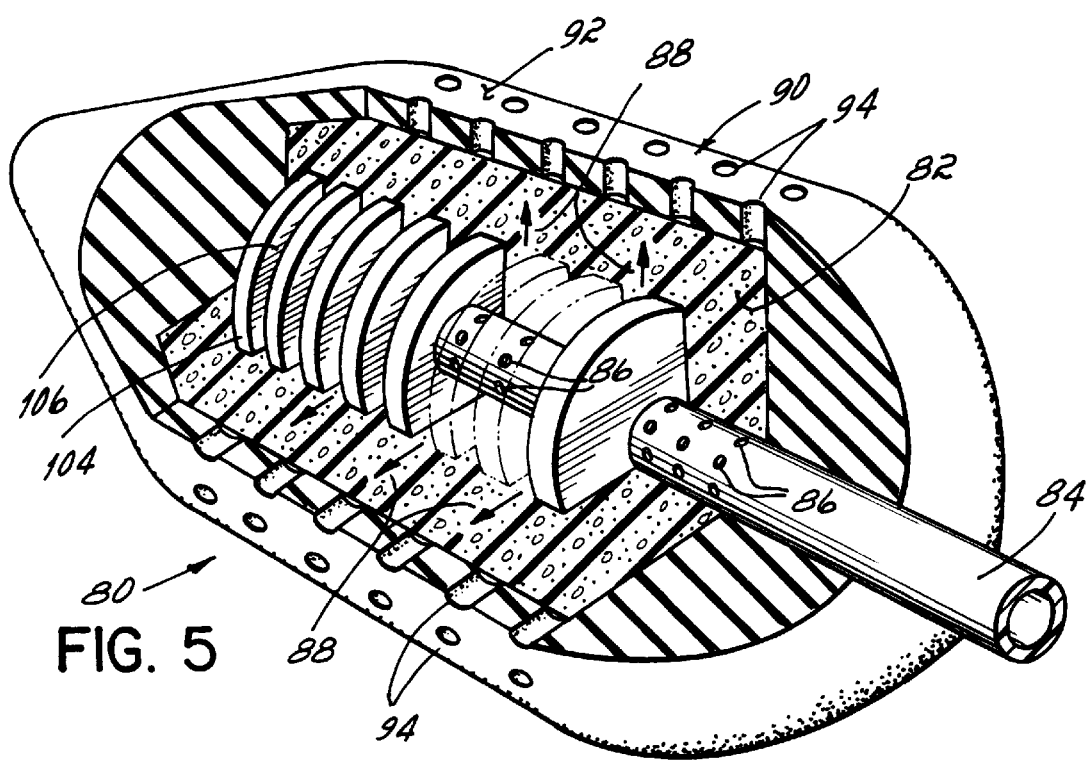
FIG. 5 is a perspective view, in partial cross-section, of an alternative embodiment of the dispenser head of the present invention.

FIG. 5 illustrates an alternative dispenser head to be used with the infusor 10 of the invention. More specifically, dispenser head 80 comprises a porous fiber core 82 which surrounds an end of the delivery tube 84 having a plurality of apertures 86 formed therein. As medication is dispensed into core 82 through apertures 86, the core 82 is operable to direct the medication radially outward from tube 84 to the outside of a core as designated by arrows 88. A shell 90 surrounds core 82 and tube 84. The shell 90 is preferably stiffer than core 82 and the outer surface 92 of shell 90 defines the contact surface for contacting the mucous membrane. A plurality of apertures 94 are formed within shell 90 for dispensing medication from core 82. Preferably, shell 90 is also porous such that medication from core 82 is wicked away from the core and onto the contact surface 92 to be absorbed by the mucous membrane. Dispenser head 80 is preferably lightweight and dimensioned to fit snugly within a rectal cavity without creating a strong gravitational sensation within the rectal cavity such that the body seeks to expel the dispenser head 80.

Figure 6A:
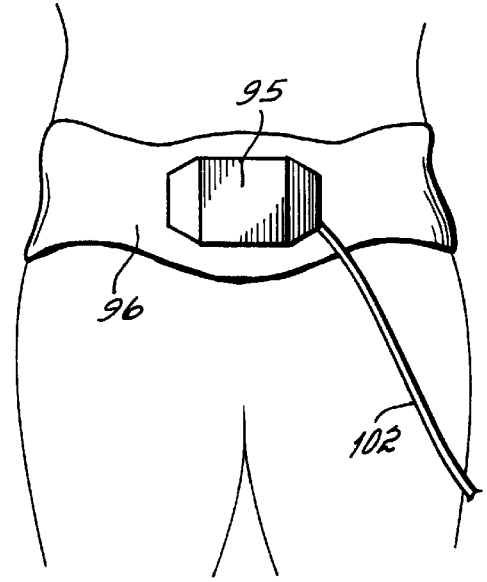
FIG. 6A is a front view of a magnetic element of the infusor system utilized with the dispenser head illustrated in FIG. 5.
Figure 6B:
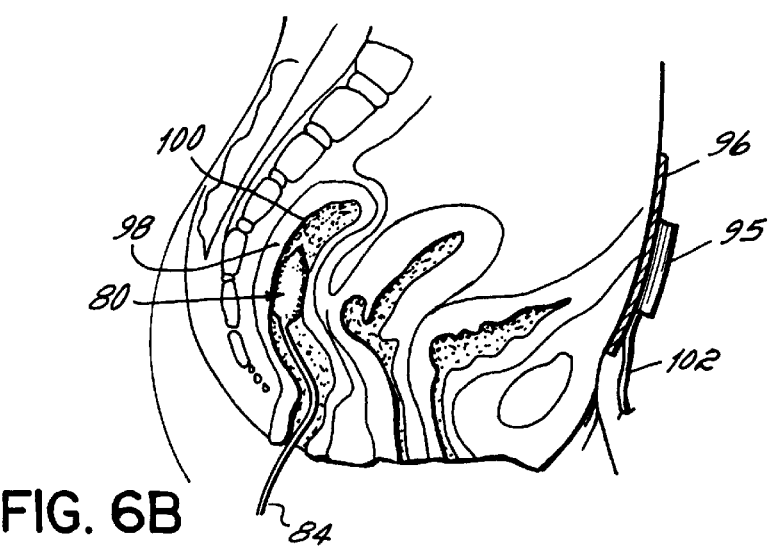
FIG. 6B is a side view of a patient's body, in partial cross-section of a patient body, utilizing the dispenser head of FIG. 5 and the magnetic element of FIG. 6A.

Dispenser head 80 is utilized in conjunction with a magnetic element which is attached to a portion of a body for securing the dispenser head 80 within the rectal cavity (see FIG. 6A) More specifically, the magnetic element 95 is fixed to a portion of the body, such as by a belt 96 or other means. Magnetic element 95 is shown attached with belt 96 around a waist of a patient to operate in conjunction with dispenser head 80 within the anal cavity 98 of a patient to dispense medication against mucous membrane 100. The magnetic element may be a permanent magnet or might be an electromagnet as illustrated in FIG. 6A which is coupled to an appropriate power source (not shown) by conductor line 102. Referring again to FIG. 5, dispenser head 80 includes a ferrous material therein and preferably includes a cylindrical structure of ferrous material 104, such as a cylinder of light weight ferrous plastic, which surrounds the end of tube 84 and is generally coaxial therewith. The elongated cylindrical structure 104 includes slots 106 therein which would allow the medication to pass through the cylindrical structure 104 as it travels from the apertures 86 to the apertures 94 of shell 90. As illustrated in FIG. 6B, when the magnetic element 95 is placed on the body proximate to the body cavity 98 containing dispenser head 80, there is a magnetic attraction between the magnetic element 95 and the ferrous material 104 of the dispenser head 80. The magnetic attraction holds the dispenser head 80 secure within the body cavity during use. Magnetic attraction further provides positive contact between the contact surface 92 of dispenser head 80 and mucous membrane 100 so that medication may be effectively administered.

FIGS. 6A and 6B illustrate use of the infusor within the rectal cavity 98 and therefore the magnetic element 95 is positioned around the waist with belt 96. As will be appreciated by a person of ordinary skill in the art, the infusor system 10 of the invention may be utilized in a number of different body cavities to contact a mucous membrane. Accordingly, the magnetic element 95 and the securing structure 96 may be configured for positioning on other parts of the body depending upon where the body cavity of interest is located.

Figure 7A:
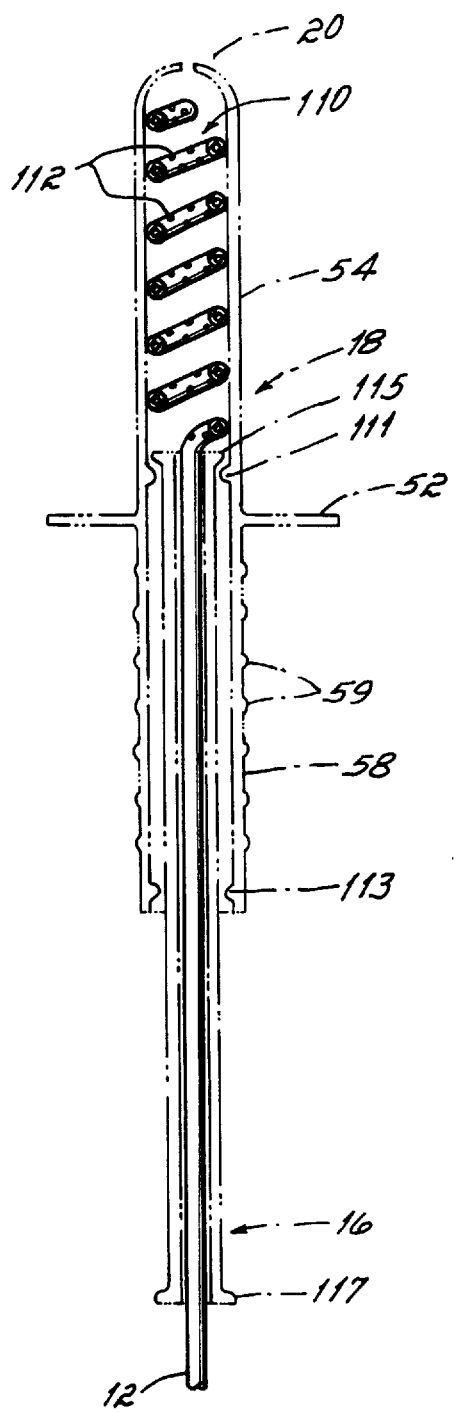
Figure 7B:
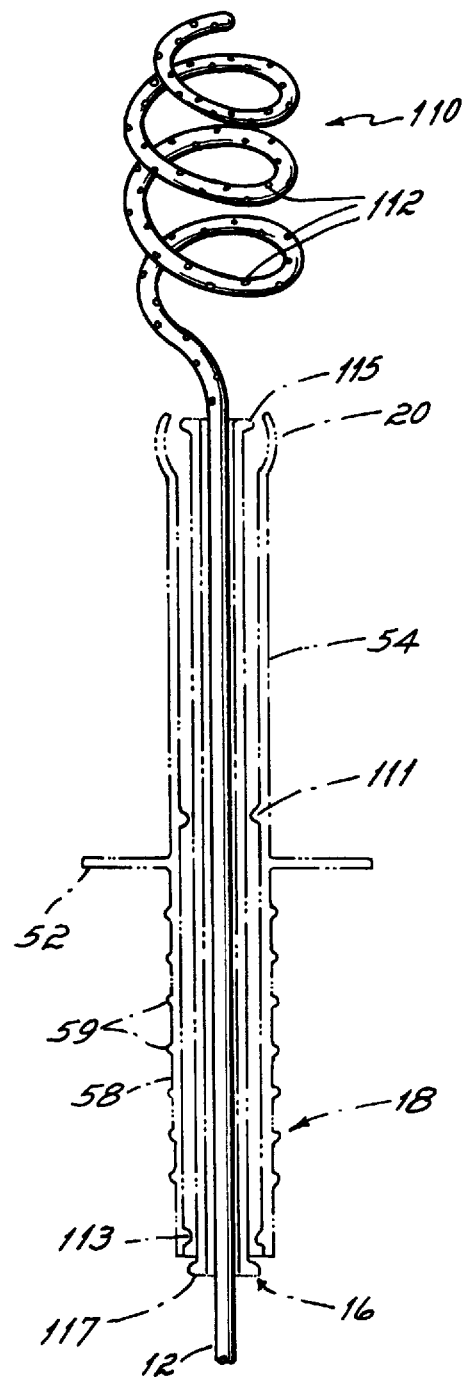
FIG. 7B is a side cross-sectional view of the dispenser head of FIG. 7A with the sheath retracted and the dispenser head expanded.

FIGS. 7A and 7B illustrate a further alternative embodiment of the infusor of the present invention. As illustrated in FIG. 7A, the dispenser head includes a coiled element 110 which is wound in an elongated shape and includes a plurality of medication-dispensing apertures 112 formed therein. When the coil element 110 is surrounded by a sheath 18, it is held in a compressed state for application into the body cavity (see FIG. 7A). Upon projecting the coil element 110 out of the end of sheath 18 with plunger 16, the coil element 110 then expands in diameter to form a generally elongated cylindrical structure to contact a mucous membrane. The sheath 18 has an upper detent 111 which encircles the plunger 16 and a lower detent 113 which also encircles the plunger. The detents 111, 113 keep plunger 16 aligned and also act against end ridges 115, 117 on the plunger to contain the plunger 16 in the sheath 18. The outer surfaces of the loops of coil element 110 provide a contact surface and medication is dispensed through tube 12 and onto the contact surfaces of the coil 110 through apertures 112. Therefore, coil element 110 is appropriately coupled to medication delivery tube 12. The coil element in an expanded state is preferably configured to fit snugly within the rectal cavity or other body cavity of a patient and is preferably made of a lightweight material which is sufficiently strong enough to maintain its expanded shape within the body cavity. Preferably, however, the coil is not too rigid, in order to avoid abrading the delicate mucous membrane. Coil element operates in accordance with the principles of the invention as discussed hereinabove.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. An infusor system for administering medications to a mucous membrane in the body of a patient comprising:

a flexible, elongated delivery tube with opposite ends, one of said ends couplable to a supply of liquid medication, the tube extending in length such that said one end is couplable to a medication supply remote from the patient mucous membrane;

a dispenser head coupled to another end of the delivery tube, the dispenser head including a plurality of troughs and contact surfaces and configured to be placed within a body cavity of a patient body such that the contact surfaces contact a portion of a mucous membrane in the body, the troughs being adjacent to the contact surfaces on the dispenser head and being operable for directing medication from the delivery tube along the dispenser head for delivery to the contact surfaces so that the medication may be absorbed by the mucous membrane and distributed in the body of the patient.

2. The infusor system of claim 1 wherein the delivery tube comprises a plurality of apertures formed in the end of the tube coupled to the dispenser head for spreading medication into the troughs and over the contact surfaces of the dispenser head for efficient distribution of the medication to the mucous membrane.

3. The infusor system of claim 1 wherein a portion of the dispenser head is formed of a porous material for wicking the medication delivered by the tube and directing the medication to the troughs and throughout the portion of the head and to the contact surfaces.

4. The infusor system of claim 3 where the dispenser head portion comprises open-cell foam material.

5. The infusor system of claim 1 wherein the dispenser head includes passages formed in the head to extend generally between the delivery tube and the troughs and contact surfaces to direct medication from the tube to the troughs and contact surfaces.

6. The infusor system of claim 1 further comprising a wicking membrane on a portion of one of the contact surfaces, the wicking membrane operable to carry medication from the contact surface to the mucous membrane.

7. The infusor system of claim 1 further comprising an elongated plunger coupled to the dispenser head for facilitating placement of the head in the body cavity adjacent a mucous membrane.

8. The infusor system of claim 1 further comprising a sheath configured for surrounding the dispenser head and covering the head, the sheath slidable with respect to the head for sliding away from the head when in the body cavity for creating contact between the mucous membrane and the contact surface.

9. The infusor system of claim 8 wherein the sheath is configured to be removed from the infusor when the dispenser head has expanded within the body cavity.

10. The infusor system of claim 8, the sheath including a tear away portion for being torn away from the sheath to remove the sheath from the infusor when the dispenser head is placed in the body cavity.

11. The infusor system of claim 1 wherein the dispenser head is formed of a resilient compressible material and is operable for compressing when being placed within the body cavity and expanding from a compressed state when in a body cavity to provide positive contact between the mucous membrane and the dispenser head contact surface.

12. The infusor system of claim 11 further comprising a sheath configured for surrounding the dispenser head and maintaining the head in a compressed state when being placed within the body cavity, the sheath slidable with respect to the head for sliding away from the head when in the body cavity to allow the head to expand.

13. The infusor system of claim 1 further comprising a one-way valve positioned in the delivery tube to create one-way flow of medication in the tube from the medication supply to the dispenser head.

14. The infusor system of claim 1 further comprising an injection dock positioned in the delivery tube for receiving a syringe for injecting bolus dosages of medication into the dispenser head.

15. The infusor system of claim 1 further comprising a disposal package slidably coupled to the delivery tube, the package operable for being slid over the tube to cover the dispenser head when it is removed from the body cavity for safe disposal of the infusor system.

16. The infusor system of claim 1 wherein the dispenser head further includes a ferrous element, the infusor system further comprising a magnetic device, the magnetic device positionable on the patient body proximate the body cavity containing the dispenser head and operable to magnetically attract the ferrous element to maintain the dispenser head in the cavity and against the mucous membrane.

17. The infusor system of claim 1 further comprising a marker located on the delivery tube for indicating the insertion depth of the dispenser head within the body cavity to ensure proper placement of the contact surfaces to contact the mucous membrane.

18. The infusor system of claim 17 wherein the marker includes a section of the delivery tube adjacent the dispenser head which is colored a different color than another section of the tube adjacent a supply of medication.

19. The infusor system of claim 1 further comprising a radio-opaque marker positioned on one of the dispenser head and the tube for electronically indicating, through electronic detection equipment, the insertion depth of the dispenser head within the body cavity to ensure proper placement of the contact surface to contact the mucous membrane.

20. The infusor system of claim 1 wherein said dispenser head is stellate in shape including a plurality of alternating troughs and contact surfaces.

21. The infusor system of claim wherein said dispenser head includes at least one fin extending outwardly on the dispenser head from the delivery tube, one of said contacts surfaces being positioned on said fin.

22. The infusor system of claim 21 wherein said at least one fin is foldable around a portion of said dispenser head for compressing the dispenser head to insert it into a mucous membrane.

* * * * *

UNITED STATES PATENT AND TRADEMARK OFFICE
CERTIFICATE OF CORRECTION

PATENT NO. : 5,846,216
DATED : December 8, 1998
INVENTOR(S) : Gilbert Gonzales, David A. Easter, Douglas E. Boyd and Kenneth E. Hughes It is certified that error appears in the above-identified patent and that said Letters Patent is hereby corrected as shown below:

In Column 1, line 55, delete the word "chose" and insert --choose--.

In Column 6, line 20, delete the letter "a" before the word "different".

In Column 8, line 56, delete "is illustrated" and insert --as illustrated--.

In Column 10, lines 4 and 5, delete "embodiment of invention. The" and insert — embodiment of the invention, the--

In Column 12, line 27, delete "address" and insert --addressing--.

In Column 16, line 47, insert --1— between "claim" and "wherein".

In Column 16, line 50, delete "contacts" and insert --contact--.

Signed and Sealed this

Tenth Day of August, 1999

Attest:

Q. TODD DICKINSON

Attesting Officer

Acting Commissioner of Patents and Trademarks